United States Patent [19]

Libin

[11] Patent Number: 5,401,234
[45] Date of Patent: Mar. 28, 1995

[54] INTRAORAL APPLIANCE TO IMPROVE VOICE PRODUCTION

[76] Inventor: Barry M. Libin, 15 Thornhedge Rd., Bellport, N.Y. 11713

[21] Appl. No.: 169,355

[22] Filed: Dec. 20, 1993

[51] Int. Cl.$^6$ ................................................ A61F 5/56
[52] U.S. Cl. ...................................... 600/24; 433/140; 128/861
[58] Field of Search ................. 128/859, 861; 601/38; 602/17, 902; 433/6, 140; 600/23, 24

[56] References Cited

U.S. PATENT DOCUMENTS

| | | | |
|---|---|---|---|
| 584,696 | 6/1897 | Monday | 600/24 |
| 3,223,085 | 12/1965 | Gores et al. | 128/861 |
| 4,457,708 | 7/1984 | Dufour | 433/6 |
| 4,519,386 | 5/1985 | Sullivan | 128/859 |
| 4,573,919 | 3/1986 | Sinkora | 433/140 |
| 4,671,766 | 6/1987 | Norton | 433/6 |
| 4,799,500 | 1/1989 | Newbury | 128/859 |
| 5,018,533 | 5/1991 | Hawkins | 128/859 X |
| 5,203,701 | 4/1993 | Burteh | 433/6 X |

Primary Examiner—Richard J. Apley
Assistant Examiner—Linda C. M. Dvorak
Attorney, Agent, or Firm—Michael Ebert

[57] ABSTRACT

An intraoral appliance which when worn by a singer or other vocalist acts to improve the quality of the voice and increase its power. The appliance is constituted by a pair of spacer pieces molded to conform to select teeth in the oral cavity of the vocalist, the pieces being seated on molars or other teeth on opposing sides of either the upper or the lower dental arch. The smooth head surfaces of the pieces are raised slightly above the teeth on which they are seated to prevent the arches from meeting and causing the mandible supporting the lower arch to slide forward relative to the maxilla to an extent limited by the parameters of the temporomadibular joint. The displaced mandible serves to release tension on the muscles of the head, neck and chest associated with the mandible, giving rise to greater and more efficient respiration, a relaxation of the hyoid bone supporting the tongue and its muscles and from which the larynx is suspended, and a relaxation of the vocal cords of the larynx. The changes in tongue, cheek, lip and cranial bone positions resulting from displacement of the mandible, enhance the resonance of the voice and impart greater power thereto.

8 Claims, 2 Drawing Sheets

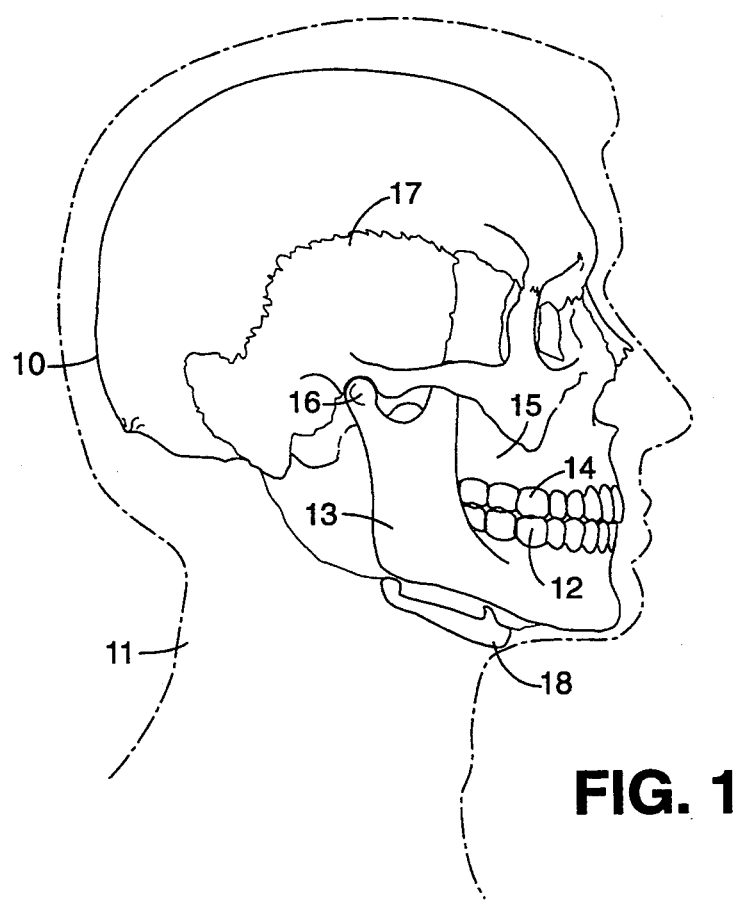
FIG. 1
FIG. 2
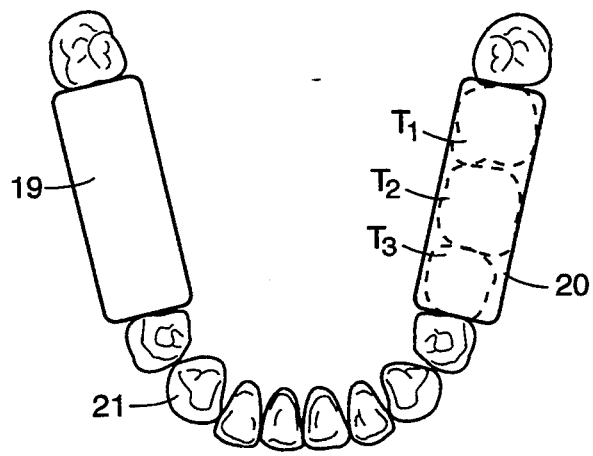
FIG. 3
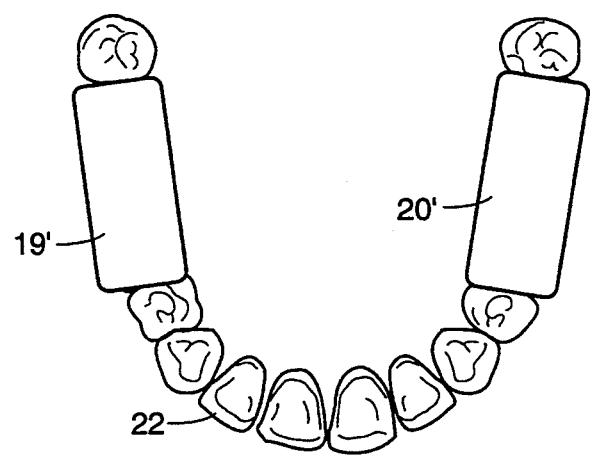

INTRAORAL APPLIANCE TO IMPROVE VOICE PRODUCTION

BACKGROUND OF INVENTION

1. Field of Invention

This invention relates generally to an intraoral appliance which when worn by a vocalist acts to improve voice production, and more particularly to an appliance for this purpose constituted by a pair of spacer pieces molded to conform to selected teeth in the oral cavity of the vocalist, the pieces being seated on the molars or other teeth on opposing sides of the upper or lower dental arch to prevent these arches from meeting and causing the mandible supporting the lower arch to slide forward relative to the maxilla, thereby releasing tension on the muscles associated with the mandible.

2. Status of Prior Art

The trachea is the main trunk of a system of tubes by which air passes to and from the lungs. The respiratory system which includes the lungs functions to inhale and exhale air through the trachea. The larynx is the modified upper section of the trachea and contains the vocal cords. These include a pair of vocal folds that when drawn taut and subjected to a flow of breath, then vibrate to produce the sounds of the voice. In the context of the human voice, resonance refers to the quality imparted to sound vibrations originating in the larynx by resonator chambers formed by the oral and nasal cavities. The power or amplitude of the voice depends on respiration.

The larynx is composed of four principal cartillages: the thyroid, the cricold, the arytenoid and the epiglottis. These cartillages are controlled by three primary groups of muscles. When contracted, the cricothyroid muscle brings the cricoid and thyroid cartillages together, thereby stretching the vocal cords to control the pitch of the vibrations produced thereby. The tension on the vocal cords is primarily controlled by the thyroarytenoid muscle, while three sets of arytenoid muscles are involved with vocal cord adduction.

The proper balance of the muscles of the larynx is essential to effective vocalization. The laryngeal mechanism is a precision instrument requiring critical muscular tensions and cartillage positions to produce optimum sounds.

The larynx is suspended from the hyoid bone disposed in the throat between the thyroid cartillage and the roof of the tongue. The hyoid bone is linked by muscles to the mandible or lower jaw. The tension on these muscles is a function of the position of the mandible, and has a strong influence on the behavior of the larynx. The present invention provides an intraoral appliance which exploits the relationship between mandible position and voice production to significantly improve the ability of a vocalist to produce sounds of fine quality and high amplitude.

The mandible on which the teeth of the lower dental arch are anchored is the horseshoe-shaped bone of the lower jaw which articulates with the skull at the temporomandibular joint (TMJ). This joint includes a mandibular condyle which is a rounded U-shaped protruberance at the rear end of the lower jaw that is articulated to the temporal bone of the cranium to create a joint.

A properly functioning TMJ is virtually free of friction and sound, and produces no pain as the joint operation. Joint operation is facilitated by a smooth disc that rides between the condyle and the temporal bone, the disc being surrounded by a synovial fluid; a clear, thick lubricant. As the mouth proceeds to open, the condyle first rotates against the disc, and with full opening, it then glides forward with the disc. Thus the TMJ first acts as a rotating joint having a fixed pivot point, and then as a translatory joint having a sliding pivot point. The extent to which the mandible can slide forward relative to the maxilla is determined by the parameters of the joint.

Injury to the TMJ often results in a tendency of the joint disc to become misaligned with the mandibular condyle, or in a relationship which forces synovial fluid out of the joint space, thereby starving the disc of the lubricant needed for proper operation. Many professional vocalists impose very heavy demands on the mandible, when for example a singer performs vocal exercises for many hours with mandibular movements bordering upon the extremes of its physiologic range. The disc-condyle relationship may then suffer injury, and voice production will be impaired.

Mandibular motion is energized by the muscles that link the mandible above to the bones of the face and cranium, and below to the neck, including the hyoid bone, clavicle and sternum. Healthy mandibular movement for effective vocalization mandates a neurophysiologic integration of all of the muscles and bones involved in carrying out this function.

A common condition affecting professional vocalists is craniomandibular-cervical muscular dysfunction resulting from sprain of the muscles connecting the mandible to the head and neck. This dysfunction adversely affects the quality of the voice and also may cause head, facial and ear pains. Because the major muscles involved in voice production are strongly influenced by mandibular position, a craniomandibular-cervical muscular dysfunction can result in hoarseness and chronic voice irritation which interfere with the ability of the vocalist to produce sounds of good quality and high amplitude.

SUMMARY OF INVENTION

The main object of this invention is to provide an intraoral appliance which when worn by a speaker, actor, singer or other vocalist, acts to improve the quality of the sounds produced by the vocalist and to increase their power.

More particularly, an object of this invention is to provide an intraoral appliance which when worn by a vocalist, causes forward displacement of the mandible relative to the maxilla to an extent limited by the TMJ, this displacement resulting in the relaxation of the craniomandibular-cervical muscles which govern the components involved in voice production.

A significant advantage of the invention is that it not only functions to improve voice production but it also reduces the possibility of temporomandibular joint derangement and craniomandibular-cervical muscular dysfunction.

Briefly stated, these objects are attained by an intraoral appliance which when worn by a singer or other vocalist acts to improve the quality of the voice and increase its power. The appliance is constituted by a pair of spacer pieces molded to conform to select teeth in the oral cavity of the vocalist, the pieces being seated on molars or other teeth on opposing sides of either the upper or the lower dental arch. The smooth head surfaces of the pieces are raised slightly above the teeth on which they are seated to prevent the arches from meeting and causing the mandible supporting the lower arch to slide forward relative to the maxilla to an extent limited by the parameters of the temporomandibular joint.

The displaced mandible serves to release tension on the muscles of the head, neck and chest associated with the mandible, giving rise to greater and more efficient respiration, a relaxation of the hyoid bone supporting the tongue and its muscles and from which the larynx is suspended, and a relaxation of the vocal cords of the larynx. The changes in tongue, cheek, lip and cranial bone positions resulting from displacement of the mandible, enhance the resonance of the voice and impart greater power thereto.

BRIEF DESCRIPTION OF DRAWINGS

For a better understanding of the invention, as well as further features thereof, reference is made to the detailed description thereof to be read in connection with the annexed drawings wherein:

FIG. 1 schematically illustrates the head and neck of the vocalist to be fitted with an appliance in accordance with the invention, this figure showing the temporomandibular joint;

FIG. 2 illustrates the appliance formed by a pair of spacer pieces fitted onto the lower dental arch of the vocalist;

FIG. 3 illustrates the appliance fitted onto the upper dental arch of the vocalist;

DETAILED DESCRIPTION OF INVENTION

Figure 4:
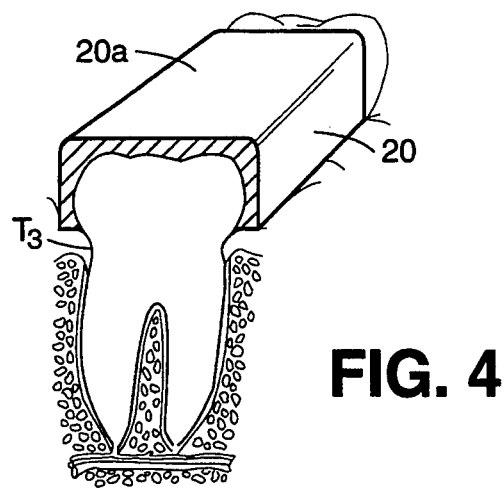
FIG. 4 shows one of the pieces seated on a molar.

Referring now to FIG. 1, this figure schematically shows the head 10 and neck 11 of a vocalist who is to be fitted with an intraoral appliance in accordance with the invention to improve voice production and to reduce the possibility of temporomandibular joint derangement and craniomandibular-cervical muscular dysfunction.

As shown in this figure, when the vocalist's mouth is closed, the teeth on the lower dental arch 12 which are anchored on the lower jaw or mandible 13 normally meet and make tooth-to-tooth contact with corresponding teeth of the upper dental arch 14 whose teeth are anchored on the upper jaw or maxilla 15.

Mandible 13 is provided at its rear end with a mandibular condyle 16. The condyle is articulated to the temporal bone 17 of the cranium, the temporomandibular joint (TMJ) being at the junction of the condyle and the temporal bone. Disposed in neck 11 below mandible 13 is the hyoid bone 18 which supports the tongue and its muscles, the larynx being suspended by muscles from the hyoid bone.

As previously explained, the TMJ is really two joints, for as the mouth opens it first functions as a rotary joint and with full opening it then acts as a translatory joint permitting the mandible to slide forward. The intraoral appliance in accordance with this invention, when worn by a vocalist, causes the mandible to slide forward relative to the maxilla to an extent limited by the parameters of the TMJ, and in doing so releases tension on the craniomandibular-cervical muscles of the head, neck, chest which are connected to the mandible. The forward displacement of the mandible reduces tension on these muscles. As a consequence of such muscle relaxation, respiration becomes easier, greater and more efficient, and the extrinsic and intrinsic muscles of the vocal folds and larynx of the laryngeal region, as well as the muscles linked to the hyoid bone become less tense.

The resultant alterations in tongue, cheek, lip and cranial bone positions produce more physiologic positioning of these elements, all critical to voice production, and they enhance the resonance of the voice and augment its power.

The appliance, as shown in FIG. 2, is constituted by a pair of spacer pieces 19 and 20 which are molded to conform to selected teeth in the oral cavity and these pieces are snugly seated on premolar-molar teeth $T_1$, $T_2$ and $T_3$ on opposing sides of the lower dental arch 21 whose teeth are anchored on the mandible.

The technology involved in producing the spacer pieces is similar to that involved in fabricating dental crowns for teeth. The pieces are fabricated by a dental laboratory from impressions made by a dentist or technician of the first molar or pre-molar-molar teeth on opposing sides of the lower arch. The choice of teeth depends upon the dentition present in the mouth of the vocalist being fitted with the pieces, as diagnosed by the dentist.

The pieces are thin, compact and light in weight and have smooth surfaces to allow freedom from obstruction of phonetics and comfort to the tongue, lips, cheeks and other soft tissues of the mouth in contact with the pieces.

The pieces can be made of acrylic, vitallium, stainless steel or other materials that fulfill the requirement that the pieces be well fitting, light-weight and have smooth exterior surfaces free of sharp edges to prevent irritation to the oral tissues. In practice, the pieces can be provided with an acrylic coating or with a porcelain outer layer bonded thereto, to render the pieces aesthetically acceptable. Or the pieces may be coated with PTFE (TEFLON) to provide an extremely low coefficient of friction promoting a sliding action. Since the pieces are fitted on teeth at the rear of the dental arch, they are normally not seen by those observing the performing vocalist.

The pieces which snugly fit onto the teeth are retained thereon by the frictional characteristics of the interior cavity surface of the pieces which conform to the tooth surface. Retention of the pieces can be assured by adding thereto small clasps which engage the teeth adjacent to pieces.

FIG. 2 shows pieces 19 and 20 molded to fit onto the premolar-molar teeth on opposing sides of the mandibular or lower dental arch 21.

In practice, pieces 19' and 20' may be molded, as shown in FIG. 3, to fit onto the premolar-molar teeth on opposing sides of the maxillary or upper dental arch 22. While the placement of the pieces on the lower dental arch is normally preferable, in some cases because of the condition of the vocalist's teeth, it may be desirable to fit pieces to the upper arch.

As shown in FIG. 4, spacer piece 20 seated on molar $T_3$ has a smooth, flat head 20A that is slightly raised above the tooth, the head surface being smooth and having a low coefficient of friction.

Figure 5:
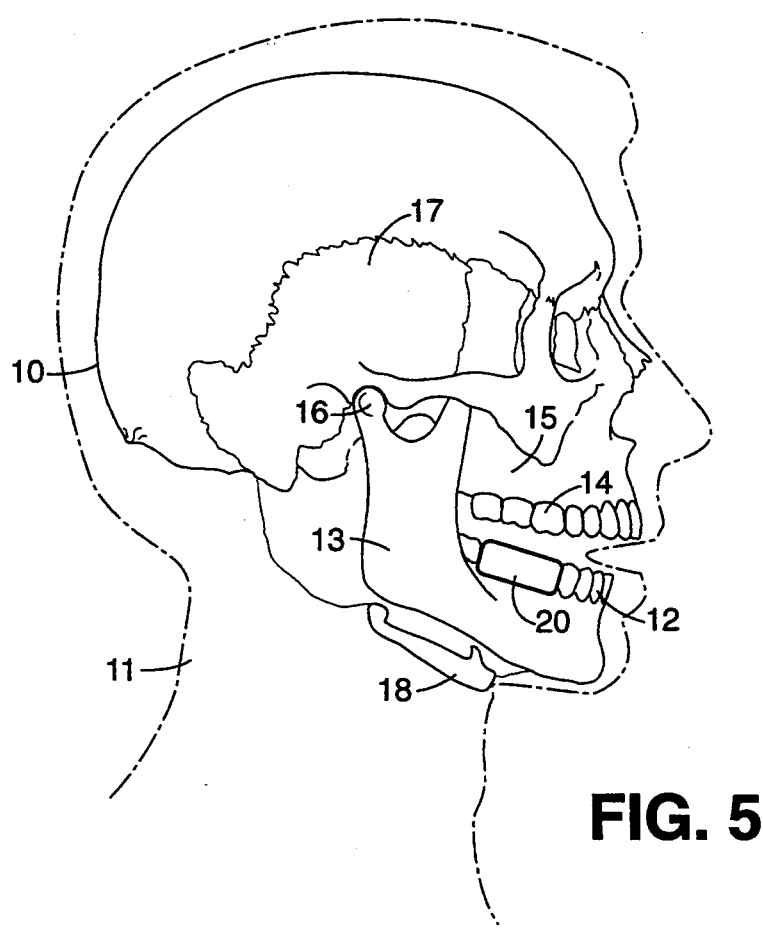
FIG. 5 schematically illustrates how the spacer pieces fitted onto teeth on the lower dental arch anchored on the mandible cause forward displacement of the mandible relative to the maxilla.

When, as shown in FIG. 5, spacer piece 20 is seated on the premolar-molar teeth on one side of the lower dental arch 21 anchored in mandible 13 whose condyle 16 is articulated to temporal bone 17 of the TMJ, the spacer piece 20 and its companion piece 19 on the opposite side of the arch then prevent the teeth on the lower arch from making contact with those of the upper arch, for when the teeth of these arches meet, the mandible is held in place.

Because of the spacer pieces, the teeth of the upper dental arch make sliding contact with the smooth flat head surfaces of the pieces and the mandible 13 supporting the lower arch is then free to slide forward relative to the maxilla to an extent limited by the sliding joint parameter of the TMJ.

The spacer pieces may be worn by the vocalist during rehearsals, vocal exercises and during performances. When the vocalist fitted with the spacer pieces opens his mouth, this causes the mandible to move forward. As a result of this movement, the mandible, tongue and its soft tissues all come forward away from the pharynx. The pharynx is a musculomembrane cavity located behind the nasal cavities, the mouth and larynx. The displacement of the mandible therefore allows greater airway space for the breath actuating the vocal chords to produce sounds.

Because the mandible is no longer held at a fixed position by tightly articulated teeth, and the spacer pieces cause the mandible to slide forward, this gives the muscles associated with the mandible an opportunity to relax. Whether relaxed to a forward, sideway or other position, the muscles above and below the mandible now experience less tension. The muscles above the mandible whose tensions are released, allow for a more relaxed face and jaw. The muscles below are also less tense not only because of the forward slide of the mandible, but also as a result of the concomitant lowering of the mandible. This shortens the distance between the mandible and the hyoid bone from which the larynx is suspended and hence the tension on the muscles which span this distance.

Release of the muscles associated with the mandible also reduces tension on the intrinsic muscles of the larynx, resulting in more balanced vocal cord relationships. Thus the vocalist's muscle upon which the vocal fold depends, is more balanced and responds to subtle movements and nuances. And the cricothyroid is then able to respond more readily when called upon to produce an increase in pitch.

Relaxation of the muscles associated with the mandible is also conducive to increased respiration, thereby providing greater support for the voice. To increase the supply of air through the larynx and its vocal folds, relaxation of the sternocleidomastoids and scalenii muscles makes possible increased inspiration. These muscles are closely associated with the cranial bones articulating with the mandible.

Thus singers who have been fitted with the spacer pieces find an increased ease in breathing. Our studies indicate a substantial increase in the voice amplitude of singers wearing the appliance without any change in the singers normal method of singing. This is due to improved resonance, and an easier ability to produce formant frequencies.

The ability to change formants and to reach the "singer's formant" make it possible for a vocalist wearing the appliance to be heard clearly in a large opera house over the sounds of a full orchestra without tiring or injuring the voice.

The major purpose of an intraoral appliance in accordance with the invention is to allow the mandible to "slide" to its most relaxed position. In effect, its covering of the irregular occlusal tooth surfaces minimizes the effect of such articulating surfaces from influencing mandibular posture. And of itself the appliance allows for a significant degree of relaxation to the upper quarter of the body. This is important because often the occlusal relationships of the teeth are improper, some surfaces of the lower teeth articulating prematurely with some of the upper teeth. This lack of unified occlusal contact results in shifting of the jaw, and imbalanced forces on the the muscles and ligaments. Thus, by being able to adjust the surface of the appliance, one can easily balance the bite upon closure, allowing any or all of the teeth to meet the overlay surface of the appliance at the same time, thereby preventing mandibular shifting, and allowing for a balanced craniomandibular-hyoid laryngeal relationship.

The height or vertical dimension of the appliance can vary. The ideal situation would be to provide a smooth, retentive, thin occlusal covering that is not esthetically detectible, nor which holds the mandible open to the point that it tires the attached muscles. Though most dentists will simply balance the occlusal tables by placing a laboratory processed, thin covering of acrylic or other material over the tooth surface, others will attempt to reach an "ideal" vertical dimension through varied techniques.

As in other restorative cases, dentists may determine vertical dimension by evaluating freeway space when the muscles are at rest, a technique often used in full denture fabrication. Others will use a "swallow" reflex to help get a more physiologically relaxed bite. Other dentists may utilize this position to be a start up point for the appliance, and utilize physical therapy to achieve full craniomandibular-cervical relaxation. In this technique, continuous adjustment to the appliance occlusal surface to allow for a balanced bite is necessary until all muscles are determined as being as fully relaxed as possible. The final vertical dimension can then utilize a "freeway" space approach, one that will not force the mandible to be opened too widely during rest. Following this final position, a registration of the mandibular position can be made by the dentist, transferred to the dental laboratory, where it can be finalized for long term use.

The objective remains, however, that the appliance cover the irregular and often improperly aligned teeth and impart a balanced occlusal position. Such an articulation will allow complete freedom for mandibular movement without the inhibiting or directing influences of the cusps, fossae or inclined planes that make up the occlusal tooth surface. Achieving the ideal vertical dimension would be the most correct. However, great improvement of voice can be achieved by simple use of a thin, properly balanced tooth overlay, which will certainly allow for a significant amount of muscular relaxation of itself, and any physical therapy techniques to further relax the musculature, followed by rebalancing of the appliance to further help in maximizing voice quality.

A dental laboratory is the preferred place to fabricate the appliance, for it will assure a properly fitting, well-contoured, smoothly finished product. All of this is essential when dealing with the professional voice. To this end an impression must be made of the teeth to be fitted with the pieces. These impressions are used to mold the pieces so that they fit snugly on the teeth.

If acrylic is the material to be used, a laboratory processed overlay is most desireable. This will reduce the chemical influence from the monomer and polymer components that can irritate the tissues from improperly cured resins. Voice irritation can occur from lack of cure. A laboratory processed appliance also allows for a maximum smoothly finished effect, reducing irritation to the tissues from a rough intraoral appliance that can be very painful, especially to the tongue of the singer, which is constantly in motion. Clasps can also be properly placed to allow for maximum retention of the appliance.

While there has been disclosed a preferred embodiment of the appliance, it will be appreciated that many changes may be made thereon without departing from the spirit of the invention.

I claim:

1. An intraoral appliance which when worn by a speaker, a singer or other vocalist having an oral cavity in which is disposed upper and lower dental arches each formed by teeth, the lower arch being supported on a mandible, which appliance acts to improve voice production, said appliance comprising a pair of spacer pieces molded to conform to selected teeth in the oral cavity of the vocalist, the pieces being adapted to be snugly seated on teeth on Opposing sides of the upper or lower dental arch to prevent the arches from meeting, said pieces each having a substantially flat head formed of a hard material having a low coefficient of friction causing the mandible supporting the lower arch to slide forward and thereby release tension on muscles associated with the mandible.

2. An appliance as set forth in claim 1, in which the pieces are adapted to be seated on premolar-molar teeth.

3. An appliance as set forth in claim 1, in which the pieces are fabricated of acrylic material.

4. An appliance as set forth in claim 1, in which the pieces are fabricated of stainless steel.

5. An appliance as set forth in claim 1, in which a porcelain layer is bonded to the exterior surface of the pieces.

6. An appliance as set forth in claim 1, in which the pieces are coated with polytetrafluoro-ethylene.

7. A method of fabricating a pair of spacer pieces as set forth in claim 1, comprising the steps of:
 A. making an impression of the teeth to be fitted with the pieces; and
 B. using these impressions to mold the pieces so that they fit snugly on the teeth.

8. An appliance as set forth in claim 1, in which each of said pieces are provided with clasps to engage the teeth to assure maximum retention of the appliance.

* * * * *